United States Patent
Kennedy

(10) Patent No.: US 9,414,602 B1
(45) Date of Patent: Aug. 16, 2016

(54) PSEUDOMONAS FLUORESCENS INHIBIT ANNUAL BLUEGRASS AND ROUGH BLUEGRASS ROOT GROWTH AND GERMINATION

(71) Applicant: The United States of America, as represented by the Secretary of Agriculture, Washington, DC (US)

(72) Inventor: Ann C Kennedy, Pullman, WA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/609,566

(22) Filed: Jan. 30, 2015

(51) Int. Cl.
*A01N 63/00* (2006.01)
*C12R 1/39* (2006.01)
*C05G 3/02* (2006.01)

(52) U.S. Cl.
CPC *A01N 63/00* (2013.01); *C05G 3/02* (2013.01); *C12R 1/39* (2013.01)

(58) Field of Classification Search
None
See application file for complete search history.

(56) References Cited

U.S. PATENT DOCUMENTS 5,332,673 A    7/1994   Harris et al.

OTHER PUBLICATIONS

Banowetz, Mark, D. et al., "Germination-Arrest Factor (GAF): Biological properties of a novel, naturally-occurring herbicide produced by selected isolates of rhizosphere bacteria", (2008) Biological Control 46:380-390.
Banowetz, Mark, D. et al., "Germination arrest factor (GAF): Part 2. Physical and chemical properties of a novel, naturally occurring herbicide produced by Pseudomonas fluorescens strain WH6q", (2009) Biological Control 50:103-110.
Gurusiddaiah, S. et al., "Isolation and Characterization of Metabolites from Pseudomonas fluorescens-D7 for Control of Downy Brome (Bromus tectorum)", (1994) Weed Science vol. 42:492-501.
Johnson, David R. et al., "Controlling Weeds with Phytopathogenic Bacteria", (1996) Weed Technology 10:621-624.
Kennedy, A.C. et al., "Rhizobacteria Suppressive to the Weed Downy Brome", (1991) Soil Science Society of America Journal 55:722-727.
Kennedy, A.C. et al., "Host range of a deleterious rhizobacterium for biological control of downy brome" (2001) Weed Science 49:792-797.
Makowski, Roberte M.D. and Mortensen, Knud, "Latent infections and penetration of the bioherbicide agent *Colletotrichum gloeosporioides* f. sp. *malvae* in non-target field crops under controlled environmental conditions", (1998) Mycological Research Journal 102(12):1545-1552.
Webster, Theodore M. and Nichols, Robert L., "Changes in the Prevalence of Weed Species in the Major Agronomic Crops of the Southern United States: 1994/1995 to 2008/2009", (2012) Weed Science 60:145-157.

*Primary Examiner* — Johann R Richter
*Assistant Examiner* — Katherine Peebles
(74) *Attorney, Agent, or Firm* — John D. Fado; David L. Marks

(57) ABSTRACT

A biocontrol agent containing one or more novel and isolated *Pseudomonas fluorescens* strains (*P. fluorescens* biovar B strain XJ3 (NRRL B-50851), *P. fluorescens* biovar B strain XS18 (NRRL B-50852), and *P. fluorescens* biovar A strain LRS 12 (NRRL B-50853)) and a biocontrol agent containing one, two or three of these bacteria with an agriculturally acceptable carrier are useful for the control of annual bluegrass and rough bluegrass root growth and germination. The biocontrol agents of this invention may be applied to the soil and/or seeds in the fall with inhibition occurring in subsequent years. The biocontrol agent can also be used in combination with herbicides that can inhibit the growth and seed production of any standing annual bluegrass and/or fertilizer to stimulate growth of the desirable plant that will compete with the annual bluegrass weed and/or rough bluegrass. Methods for use of these biocontrol agents to control to growth of annual bluegrass and rough bluegrass are also provided.

15 Claims, 1 Drawing Sheet

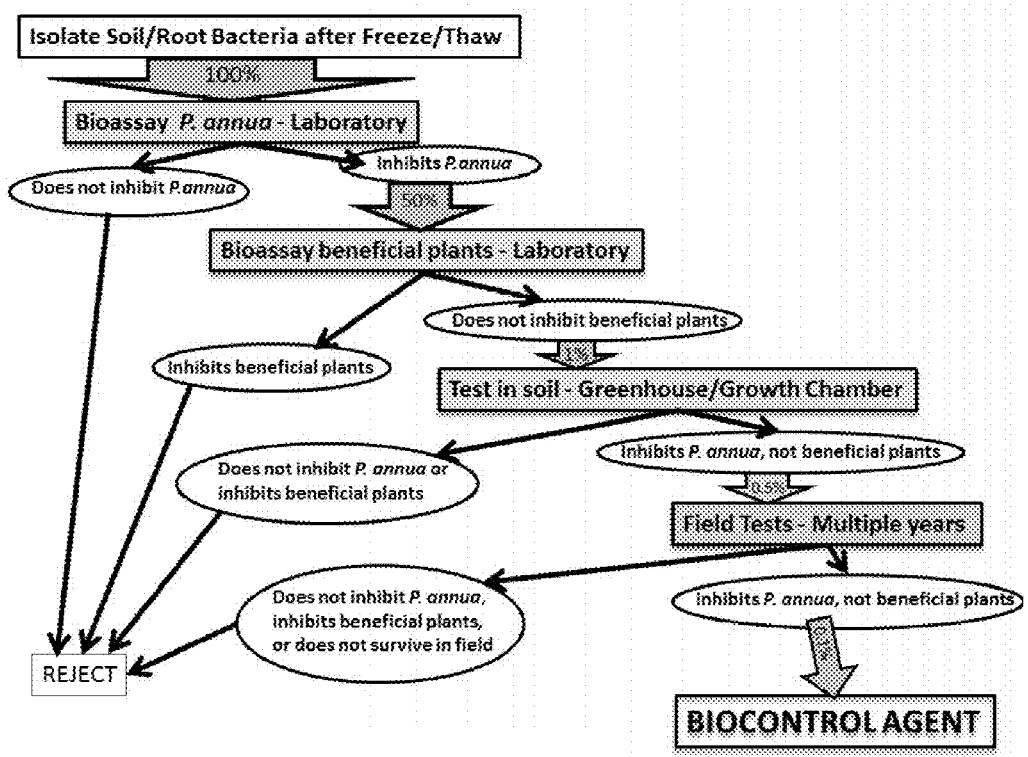

PSEUDOMONAS FLUORESCENS INHIBIT ANNUAL BLUEGRASS AND ROUGH BLUEGRASS ROOT GROWTH AND GERMINATION

BACKGROUND OF INVENTION

1. Field of Invention

This invention relates to novel isolated *Pseudomonas fluorescens* strains that have been isolated, selected, and characterized from the naturally occurring soil bacterial populations because they inhibit the growth of annual bluegrass (*Poa annua* L.) or inhibit the growth of both annual bluegrass (*Poa annua* L.) and rough bluegrass (*Poa trivialis*), but do not inhibit the growth of desired grasses, such as turfgrasses, cereal crops, and native plants. This invention also relates to novel compositions that contain the novel *Pseudomonas fluorescens* strains described herein. In addition this invention relates to methods of using the novel, isolated *P. fluorescens* strains and the novel compositions, alone or in combination with other *P. fluorescens* strains, herbicides, and/or fertilizers.

2. Description of the Prior Art

Annual bluegrass (*Poa annua* L.) is a cool-season annual grass that is a major weed species in turf, turfgrass seed production, and golf courses of the western United States (Webster and Nichols, 2012 *Weed Science* 60(2):145-157). Annual bluegrass germinates in late summer or fall as soil temperatures fall below 70° F. It continues to germinate throughout winter, allowing several flushes of germination at any one site throughout the season. The life cycles of annual bluegrass and turfgrass are very similar, and annual bluegrass is often more competitive than most turfgrasses. Because annual bluegrass is a grass weed growing with turfgrass, selective control is difficult. Pre-emergent herbicides, such as benefin, bensulide, dithiopyr, oryzalin, oxadiazon, pendimethalin, prodiamine, and benefin/oryzalin, are successful in limiting germination of annual bluegrass. A few post-emergent herbicides reduce *Poa annua* L. growth, but they could also kill desirable turfgrasses. As such, usage of these post-emergent herbicides are limited. For example, foramsulfuron, sulfosulfuron, and trifloxysulfuron can be used only on warm-season turfgrass. Ethofumesate can be used in dormant bermudagrass, creeping bentgrass, Kentucky bluegrass, tall fescue, perennial ryegrass, and St. Augustine to reduce annual bluegrass infestations. Pronamide can be used in warm-season turfgrass for established annual bluegrass, but it is slow acting. Golf-course managers have few tools to combat *Poa annua* L. and the invasion of this weed often means that greens must be ripped out and replaced every ten years.

Rough bluegrass (*Poa trivialis*) is also a cool-season annual grass that is a major weed species. Similar to annual bluegrass, rough bluegrass can outcompete turfgrasses and native plants.

Use of antagonistic microorganisms as bioherbicides against some weeds has been previously reported (Kennedy, et al., 1991, *Soil Sci. Soc. Amer. J.* 55:722-727; Kennedy, et al., 2001, *Weed Sci.* 49:792-797; Makowski and Mortensen, 1998, *Mycol. Res.* 102(12):1545-1552). *Xanthomonas campestris* pv. *poannua* is sprayed on plant leaves during mowing and reduces annual bluegrass in bermudagrass. The bacterium enters the plant through the cut leaf and causes systemic wilt, which kills the plant (Johnson, et al., 1996, *Weed Technology*, 10(3):621-624). A germination arrest factor (GAF) produced by *Pseudomonas fluorescens* strain WH6 and other related species produce a compound that in-vitro reduced germination of grassy weed species including annual bluegrass (Banowetz, et al., 2008, *Biological Control* 46:380-390; Banowetz, et al., 2009, *Biological Control* 50:103-110.) However, *P. fluorescens* strain WH6 and other related species failed to reduce germination of annual bluegrass in the field. GAF failed to inhibit germination of grassy weed species in the field and the selectivity of GAF is not known.

The physiological characteristics required for a bacterial strain to suppress annual weeds are specific as to (1) the weed growth to be controlled; (2) the specificity of the inhibition is limited to that weed or similar weeds and lack activity against crops or economically important plants; (3) the mode of action of weed control; (4) the activity and ecological niche of the microorganism; and (5) cultural practices and soil and climatic conditions must be favorable for suppressive. Thus, information about microbial treatments for control of weeds other than annual bluegrass cannot be used to predict strains of microorganisms that would reduce annual bluegrass under field conditions or predict criteria for selecting such strains.

BRIEF DESCRIPTION OF THE INVENTION

It is an object of this invention to have three isolated and novel *Pseudomonas fluorescens* strains that are effective in controlling the root growth or the germination of annual bluegrass and/or rough bluegrass. These three strains of *P. fluorescens* are *P. fluorescens* biovar B strain XJ3 (NRRL B-50851), *P. fluorescens* biovar B strain XS18 (NRRL B-50852), and *P. fluorescens* biovar A strain LRS12 (NRRL B-50853), where *P. fluorescens* strain LRS12 (NRRL B-50853) controls the root growth or germination of both *P. annua* L. and *P. trivialis*.

It is another object of this invention to have a biocontrol agent that can control and/or inhibit annual bluegrass or can control and/or inhibit both annual bluegrass (*Poa annua* L.) and rough bluegrass root growth and seed germination and that the biocontrol agent contains *P. fluorescens* biovar B strain XJ3 (NRRL B-50851), *P. fluorescens* biovar B strain XS18 (NRRL B-50852), *P. fluorescens* biovar A strain LRS12 (NRRL B-50853), combinations thereof, and compositions containing one or more of these bacteria, *P. fluorescens* strain LRS12 (NRRL B-50853) controls and/or inhibits root growth and seed germination of both *P. annua* L. and *P. trivialis*.

It is an object of this invention to have a biocontrol agent that can control and/or inhibit annual bluegrass or can control and/or inhibit both annual bluegrass and rough bluegrass root growth and seed germination. The biocontrol agent contains *P. fluorescens* biovar B strain XJ3 (NRRL B-50851), *P. fluorescens* biovar B strain XS18 (NRRL B-50852), or *P. fluorescens* biovar A strain LRS12 (NRRL B-50853), or combinations thereof, where *P. fluorescens* strain LRS12 (NRRL B-50853) controls and/or inhibits root growth and seed germination of both *P. annua* L. and *P. trivialis*. The concentration of the bacteria applied to the treated land ranges between approximately $10^5$ to approximately $10^{11}$ cfu bacteria per square meter of treated land. For one alternative embodiment, if one single bacterial strain is present in the biocontrol agent, the bacteria's concentration is approximately $10^8$ cfu bacteria per square meter of treated land. For another alternative embodiment, if two or all three strains of bacteria are present in the biocontrol agent, the concentration for each strain of bacteria ranges from approximately $10^7$ to approximately $10^8$ cfu bacteria per square meter of treated land. It is another object of this invention that the biocontrol agent contains a herbicide and/or a fertilizer.

It is an object of this invention to have a biocontrol agent that can control and/or inhibit annual bluegrass or can control and/or inhibit both annual bluegrass and rough bluegrass root growth and seed germination and that the biocontrol agent contains an agriculturally acceptable carrier and either *P. fluorescens* biovar B strain XJ3 (NRRL B-50851), *P. fluorescens* biovar B strain XS18 (NRRL B-50852), or *P. fluorescens* biovar A strain LRS12 (NRRL B-50853), or combinations thereof, where *P. fluorescens* strain LRS12 (NRRL B-50853) controls and/or inhibits root growth and seed germination of both *P. annua* L. and *P. trivialis*. It is further object of this invention that the biocontrol agent can optionally contain a herbicide and/or a fertilizer. It is another object of this invention that the agriculturally acceptable carrier can be a seed from one or more desired plants, rice, talc, one or more carbohydrates, one or more polysaccharides, one or more polymeric porous materials, milk, water, medium, and pellets made from a cereal grain flour or meal. The concentration of the bacteria applied to the treated land ranges between approximately $10^5$ to approximately $10^{11}$ cfu bacteria per square meter of treated land. For one alternative embodiment, if one single bacterial strain is present in the biocontrol agent, the bacteria's concentration is approximately $10^8$ cfu bacteria per square meter of treated land. For another alternative embodiment, if two or all three strains of bacteria are present in the biocontrol agent, the concentration for each strain of bacteria ranges from approximately $10^7$ to approximately $10^8$ cfu bacteria per square meter of treated land.

It is another object of this invention to have a method for controlling the growth of annual bluegrass and/or rough bluegrass in an area in need of treatment by applying a biocontrol agent in an amount effective to control the growth of annual bluegrass and/or rough bluegrass to the area. It is a further object of this invention that the biocontrol agent contains *P. fluorescens* biovar B strain XJ3 (NRRL B-50851), *P. fluorescens* biovar B strain XS18 (NRRL B-50852), or *P. fluorescens* biovar A strain LRS12 (NRRL B-50853), or combinations thereof; and optionally a herbicide and/or a fertilizer, where *P. fluorescens* strain LRS12 (NRRL B-50853) controls the growth of both *P. annua* L. and *P. trivialis*. The concentration of the bacteria applied to the treated land ranges between approximately $10^5$ to approximately $10^{11}$ cfu bacteria per area in need of treatment. For one alternative embodiment, if one single bacterial strain is present in the biocontrol agent, the bacteria's concentration is approximately $10^8$ cfu bacteria per area in need of treatment. For another alternative embodiment, if two or all three strains of bacteria are present in the biocontrol agent, the concentration for each strain of bacteria ranges from approximately $10^7$ to approximately $10^8$ cfu bacteria per area in need of treatment. It is a further object of this invention that the application of the biocontrol agent occurs when the soil is moist (i.e., after rain or irrigation) or prior to irrigating the area in need of treatment or when rain is anticipated to occur shortly after application of the biocontrol agent. It is another object of this invention that the air temperature in the area in need of treatment should be between approximately 32° F. and approximately 70° F. in one embodiment, or between approximately 32° F. and approximately 50° F. in another embodiment, when the biocontrol agent is applied. One can apply the biocontrol agent to bare soil and/or on plants present in the area being treated. One can apply the biocontrol agent in any manner, including spraying, broadcasting, or injecting into the soil.

It is another object of this invention to have a method for controlling the growth of annual bluegrass and/or rough bluegrass in an area in need of treatment by applying a biocontrol agent in an amount effective to control the growth of annual bluegrass and/or rough bluegrass to the area. It is a further object of this invention that the biocontrol agent contains an agriculturally acceptable carrier, and *P. fluorescens* biovar B strain XJ3 (NRRL B-50851), *P. fluorescens* biovar B strain XS18 (NRRL B-50852), or *P. fluorescens* biovar A strain LRS12 (NRRL B-50853), or combinations thereof; and optionally a herbicide and/or a fertilizer, where *P. fluorescens* strain LRS12 (NRRL B-50853) controls the growth of both *P. annua* L. and *P. trivialis*. It is another object of this invention that the agriculturally acceptable carrier can be a seed from one or more desired plants, rice, talc, one or more carbohydrates, one or more polysaccharides, one or more polymeric porous materials, milk, water, medium, and pellets made from a cereal grain flour or meal. The concentration of the bacteria applied to the treated land ranges between approximately $10^5$ to approximately $10^{11}$ cfu bacteria per area in need of treatment. For one alternative embodiment, if one single bacterial strain is present in the biocontrol agent, the bacteria's concentration is approximately $10^8$ cfu bacteria per area in need of treatment. For another alternative embodiment, if two or all three strains of bacteria are present in the biocontrol agent, the concentration for each strain of bacteria ranges from approximately $10^7$ to approximately $10^8$ cfu bacteria per area in need of treatment. It is a further object of this invention that the application of the biocontrol agent occurs when the soil is moist (i.e., after rain or irrigation) or prior to irrigating the area in need of treatment or when rain is anticipated to occur shortly after application of the biocontrol agent. It is another object of this invention that the air temperature in the area in need of treatment should be between approximately 32° F. and approximately 70° F. in one embodiment, or between approximately 32° F. and approximately 50° F. in another embodiment, when the biocontrol agent is applied. One can apply the biocontrol agent to bare soil and/or on plants present in the area being treated. One can apply the biocontrol agent in any manner, including spraying, broadcasting, or injecting into the soil.

It is another object of this invention to have a kit for the control the growth of annual bluegrass and/or rough bluegrass growth, which has one or more containers containing a biocontrol agent effective in controlling annual bluegrass and/or rough bluegrass root growth or germination; optionally a container containing a herbicide; optionally a container containing a fertilizer; and instructions for applying the biocontrol agent to the area in need of treatment. The biocontrol agent contains an agriculturally acceptable carrier and one or more of the following *Pseudomonas fluorescens* strains: *P. fluorescens* biovar B strain XJ3 (NRRL B-50851), *P. fluorescens* biovar B strain XS18 (NRRL B-50852), and *P. fluorescens* biovar A strain LRS12 (NRRL B-50853), where *P. fluorescens* strain LRS12 (NRRL B-50853) controls root growth or germination of both *P. annua* L. and *P. trivialis*. It is another object of this invention that the agriculturally acceptable carrier can be a seed from one or more desired plants, rice, talc, one or more carbohydrates, one or more polysaccharides, one or more polymeric porous materials, milk, water, medium, and pellets made from a cereal grain flour or meal. The amount of *P. fluorescens* in its container is such that between approximately $10^5$ to approximately $10^{11}$ cfu *P. fluorescens* can be applied to the area to be treated. For one alternative embodiment, if one single *P. fluorescens* strain is present in the biocontrol agent, it is present in an amount such that approximately $10^8$ cfu *P. fluorescens* can be applied to the area to be treated. For another alternative embodiment, if two or all three strains of *P. fluorescens* are present in the biocontrol agent, each bacterial strain is present in an amount such that approximately $10^7$ to approximately $10^8$ cfu per bacterial strain can be applied to the area to be treated.

It is another object of this invention to have a kit for the control the growth of annual bluegrass and/or rough bluegrass growth which has one or more containers containing a biocontrol agent effective in controlling annual bluegrass and/or rough bluegrass root growth or germination; optionally a container containing a herbicide; optionally a container containing a fertilizer; and instructions for applying the biocontrol agent to the area in need of treatment. The biocontrol agent contains one or more of the following *Pseudomonas fluorescens* strains: *P. fluorescens* biovar B strain XJ3 (NRRL B-50851), *P. fluorescens* biovar B strain XS18 (NRRL B-50852), and *P. fluorescens* biovar A strain LRS12 (NRRL B-50853), where *P. fluorescens* strain LRS12 (NRRL B-50853) controls the root growth or germination of both *P. annua* L. and *P. trivialis*. The amount of *P. fluorescens* in each container is such that between approximately $10^5$ to approximately $10^{11}$ cfu *P. fluorescens* can be applied to the area to be treated. For one alternative embodiment, if one single *P. fluorescens* strain is present in the biocontrol agent, the amount in its container is such that approximately $10^8$ cfu *P. fluorescens* can be applied to the area to be treated. For another alternative embodiment, if two or all three strains of *P. fluorescens* are present in the biocontrol agent, then each bacterial strain is present in an amount such that approximately $10^7$ to approximately $10^8$ cfu per bacterial strain can be applied to the area to be treated.

BRIEF DESCRIPTION OF THE FIGURES

FIG. 1 illustrates the screening method of soil bacteria for weed-suppressive bacteria used to identify bacteria that selectively suppress *Poa annua* L. and *Poa trivialis*.

DEPOSIT OF BIOLOGICAL MATERIAL UNDER TERMS OF BUDAPEST TREATY

On Aug. 14, 2013, the inventor deposited samples of the biological materials listed in Table 1 infra and that are described and claimed herein with the U.S.D.A., Agricultural Research Service, Patent Culture Collection located at the National Center for Agricultural Utilization Research, 1815 N. University Street, Peoria, Ill. 61604, in a manner affording permanence of the deposit and ready accessibility thereto by the public if a patent is granted. These deposits have been made under the terms of the Budapest Treaty on the International Recognition of the Deposit of Microorganisms for the Purposes of Patent Procedure and the regulations thereunder.

TABLE 1

Three strains of *Pseudomonas fluorescens* and ARS Accession Number that suppress *Poa annua* L.

| Genus species/strain designation | ARS Accession Number |
|---|---|
| *Pseudomonas fluorescens* biovar B strain XJ3 | NRRL B-50851 |
| *Pseudomonas fluorescens* biovar B strain XS18 | NRRL B-50852 |
| *Pseudomonas fluorescens* biovar A strain LRS12 | NRRL B-50853 |

All restriction on the availability to the public of these biological materials identified herein and deposited as described herein will be irrevocably removed upon the granting of a patent.

The biological materials identified herein have been deposited under conditions such that access to the microorganisms are available during the pendency of the patent application to one determined by the Commissioner to be entitled thereto under 37 C.F.R. §1.14 and 35 U.S.C §122.

The deposited biological materials will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

DETAILED DESCRIPTION OF THE INVENTION

Annual bluegrass and rough bluegrass negatively affect many turfgrasses (see Table 2 for a non-limiting list of common turfgrasses) and reduce turfgrass and crop yield resulting in economic loss. Annual bluegrass and rough bluegrass outcompete desired turfgrasses and native plants by actively growing roots and germinating seeds in cold temperatures, such as between approximately 32° F. and approximately 50° F., or between approximately 32° F. and approximately 60° F., or 32° F. and approximately 70° F. Thus, during these temperature ranges a biocontrol agent for these weeds would extremely effective. After all, if one can inhibit root production by annual bluegrass and/or rough bluegrass when they are most actively growing and out-competing desired plants (e.g., turfgrass, crops, and native plants), then one can help prevent these weeds from establishing a strong root system that helps the weeds continue to out-compete the desired plants at other temperatures.

The biocontrol agent of this invention (*P. fluorescens* NRRL B-50851, *P. fluorescens* NRRL B-50852, and/or *P. fluorescens* NRRL B-50853; and/or compositions containing one or more of these bacteria) is a slow acting biocontrol agent when compared to herbicides. After application of the biocontrol agent of this invention to the soil, it may take time for the bacteria of this invention to multiply and inhibit the soil in close proximity to the weeds' roots, or reside within the intracellular spaces of the weeds' roots. While one may observe some reduction in the weeds' growth during one growing season in the treated area, it may take several growing seasons (three to four years) to observe substantial reduction in the amount of annual bluegrass and/or rough bluegrass growing in the treated area. Furthermore, one may need to reapply this biocontrol agent after five or more years for continual significant reduction in germination of the weeds that may reenter the area.

For the purposes of this invention, turfgrass is used as exemplary of a desired plant to be protected; however, the methods and compositions described herein are applicable to other grasses, crops, and native plants. Turfgrass species are present in golf courses, public parks, residential lawns, sod production facilities, sports fields, etc. in North and South America, Europe, British Isles, North Africa, North Asia, Australia, and Antarctica. Annual bluegrass (*P. annua* L.) and rough bluegrass (*P. trivialis*) negatively impact the growth, health, and viability of turfgrass. As such, it would be useful to have compositions and methods that inhibit the growth of *Poa annua* L and *P. trivialis*.

TABLE 2

Common turfgrasses in the United States.

| Common Name | Scientific Name |
|---|---|
| Alkaligrass | *Puccinellia distans* |
| Bahiagrass | *Paspalum notatum* |
| Bentgrass - Colonial | *Agrostis capillaris* |
| Bentgrass - Creeping | *Agrostis palustris* |
| Bentgrass - Spike | *Agrostis exerata* |

TABLE 2-continued

Common turfgrasses in the United States.

| Common Name | Scientific Name |
| --- | --- |
| Bermudagrass | *Cynodon dactylon* |
| Blue grama grass | *Bouteloua gracilis* |
| Bluegrass - Canada | *Poa compressa* |
| Bluegrass - Kentucky | *Poa pratensis* |
| Bluegrass - Rough | *Poa trivialis* |
| Buffalograss | *Buchloe dactyloides* |
| Carpetgrass | *Axonopus fissifolius* |
| Centipedegrass | *Eremochloa ophiuroides* |
| *Dichondra* | *Dichondra micrantha* |
| Eastern Gamagrass | *Tripsacum dactyloides* |
| Fescue - Chewings | *Festuca rubra* var. *commutate* |
| Fescue - Creeping Red | *Festuca rubra* var. *rubra* |
| Fescue - Sheeps | *Fescue ovina* var. *ovina* |
| Fescue - Tall | *Festuca arundinacea* |
| Fescue - Hard | *Festuca longifolia* |
| Grama Grass - Blue | *Bouteloua gracilis* |
| Kikuyugrass | *Pennisetum clandestinum* |
| Orchardgrass | *Dactylis glomerata* |
| Ryegrass - Perennial | *Lolium perenne* |
| Saint Augustine grass | *Stenotaphrum secundatum* |
| Seashore *Paspalum* | *Paspalum vaginatum* |
| Smooth bromegrass | *Bromus inermis* |
| Wheatgrass - Bluebunch | *Agropyron spicatum* |
| Wheatgrass - Crested | *Agropyron cristatum* |
| Zoysiagrass - *Japonica* | *Zoysia japonica* |
| Zoysiagrass - *Matrella* | *Zoysia matrella* |
| Zoysiagrass - *Tenuifolia* | *Zoysia tenuifolia* |

Chemical herbicides are well-known in the art field (see Table 3 for a non-limiting example of herbicides). However, none of the herbicides currently on the market can selectively control the growth of *P. annua* L. (annual bluegrass) without harming the desirable turfgrass. As such, the need exists for a substance/composition that can control the growth of *P. annua* L. As described herein, *P. fluorescens* NRRL B-50851, *P. fluorescens* NRRL B-50852, and *P. fluorescens* NRRL B-50853 are three bacterial strains that have been isolated from soil and selected because they control the growth and/or germination of *P. annua* L. and/or *P. trivialis* without harming the desirable turfgrass. It is noted that *P. fluorescens* strain LRS12 (NRRL B-50853) inhibits or controls the growth and/or germination of both *P. annua* L. and *P. trivialis*. The other two bacteria do not inhibit or control the growth and/or germination of *P. trivialis*.

For the purposes of this invention, the phrases "control the growth" and "control the germination" can mean inhibit the growth and/or reduce the growth of the indicated weeds and inhibit the germination and/or reduce the germination of the indicated weeds, respectively. The bacteria of the present invention exert this "control" over the weeds by inhibiting the elongation of the root cells, and thereby inhibiting or reducing root growth both during the germination process and when the seedling or plant is growing. When root growth is inhibited or reduced, the plant embryo, seedling, and plant have a more difficult time absorbing the water and nutrients needed from the soil. In turn, the growth of aerial parts of the plant is reduced. A weed with a well-established root system can usually compensate for the reduced or inhibited growth of some of its roots. As such, this invention has maximum benefits on seedlings or germinating seeds of the weeds, but can still help slow the growth of established weeds with larger root systems. Not wishing to be bound to any particular hypothesis, this invention appears to cause the weed seeds to fail to germinate because the inhibition or reduction of root cell growth and/or elongation of the embryo plant's root cells result in the embryo plant dying prior to appearance of aerial parts of the seedling.

The expressions "inhibit the growth", "inhibit the germination", and "inhibit development" of annual bluegrass (*P. annua* L.) and any similar expressions, refer to inhibition or suppression of the germination, growth, and/or development of *P. annua* L. When the annual bluegrass seed or seedlings are treated with the biocontrol agents of this invention (*P. fluorescens* strains described herein or compositions containing the *P. fluorescens* strains described herein) at least approximately 20% reduction in root growth (as measured by root dry weight) occurs compared to untreated weed seedlings and/or seeds. In other embodiments, inhibition of annual bluegrass occurs when weed seedlings and/or seeds treated with the biocontrol agents of this invention have at least approximately 25% reduction in root growth (as measured by root dry weight) compared to untreated weed seedlings and/or seeds. In another embodiment, inhibition of annual bluegrass occurs when weed seedlings and/or seeds treated with the biocontrol agents of this invention have at least approximately 30% reduction in root growth (as measured by root dry weight) compared to untreated weed seedlings and/or seeds.

In an alternative embodiment, inhibition of annual bluegrass or rough bluegrass occurs when the weed seedlings and/or seeds treated with the biocontrol agents of this invention (*P. fluorescens* strains described herein or the compositions containing the *P. fluorescens* strains described herein) have at least approximately 20% reduction in shoot growth (as measured by shoot dry weight) compared to untreated weed seedlings and/or seeds. In yet another embodiment, inhibition of annual bluegrass occurs when weed seedlings and/or seeds treated with the biocontrol agents of this invention have at least approximately 25% reduction in shoot growth (as measured by shoot dry weight) or stand (numbers of plant $m^2$) compared to untreated weed seedlings and/or seeds. In yet still another embodiment, inhibition of annual bluegrass occurs when weed seedlings and/or seeds treated with the biocontrol agents of this invention or the compositions of this invention have at least approximately 30% reduction in shoot growth (as measured by shoot dry weight) or stand (numbers of plant $m^{-2}$) compared to untreated weed seedlings and/or seeds.

The biocontrol agents of the present invention are considered safe (that is, not having an undue adverse effect) on desirable turfgrass, crop plants or desirable native plant species when a crop or turfgrass or desirable native plant seedling and/or seed, after exposure to a biocontrol agent of the present invention, has no significant reduction in root growth (as measured by root dry weight) and/or shoot growth (as measured by shoot dry weight) or stand (as measured by numbers of plant $m^{-2}$) compared to a control crop plant seedling and/or seed. In another embodiment, the biocontrol agents of the present invention are considered safe (that is, not having an undue adverse effect) on a crop plant when a crop plant seedling and/or seed, after exposure to athe biocontrol agent of the present invention, has less than approximately 10% reduction in root growth (as measured by root dry weight) or shoot growth (as measured by shoot dry weight) or stand (as measured by numbers of plant $m^2$) compared to a control crop plant seedling and/or seed. In another embodiment, the biocontrol agents of the present invention are considered safe (that is, not having an undue adverse effect) on a crop plant when a crop plant seedling and/or seed, after exposure to a biocontrol agent of the present invention, has less than approximately 15% reduction in root growth (as measured by root dry weight) or shoot growth (as measured by shoot dry weight) or stand (as measured by numbers of plant $m^{-2}$) compared to a control crop plant seedling and/or seed. The biocontrol agents of the present invention are considered safe (that is, not having an undue adverse effect) on a crop plant when a crop plant seedling and/or seed, after exposure to a biocontrol agent of the present invention, has less than approximately 20% reduction in root growth (as measured by root dry weight) or shoot growth (as measured by shoot dry weight) or stand (as measured by numbers of plant $m^{-2}$) compared to a control crop plant seedling and/or seed.

TABLE 3

Common herbicides and fertilizers that can be applied with the *Pseudomonas fluorescens* strains to surface of soil or injected into soil.

| | | |
|---|---|---|
| Herbicide | Preemergent | Benefin |
| Herbicide | Preemergent | Bensulide |
| Herbicide | Preemergent | Dithiopyr |
| Herbicide | Preemergent | Oryzalin |
| Herbicide | Preemergent | Oxadiazon |
| Herbicide | Preemergent | Pronam |
| Herbicide | Preemergent | Prodiamine |
| Herbicide | Preemergent | Pendimethalin |
| Herbicide | Preemergent | Benefin/Oryzalin |
| Herbicide | Post emergent | Ethofumesate |
| Herbicide | Post emergent | Pronamide |
| Fertilizer | Macronutrient | Nitrogen |
| Fertilizer | Macronutrient | Phosphate |
| Fertilizer | Macronutrient | Potassium |
| Fertilizer | Macronutrient | Calcium |
| Fertilizer | Macronutrient | Magnesium |
| Fertilizer | Macronutrient | Sulfur |
| Fertilizer | Micronutrient | Iron |
| Fertilizer | Micronutrient | Zinc |
| Fertilizer | Micronutrient | Molybdenum |
| Fertilizer | Micronutrient | Boron |
| Fertilizer | Micronutrient | Copper |
| Fertilizer | Macronutrient | Lime |
| Fertilizer | Organic Amendment | Bone Meal |

The biocontrol agents of this invention contain one or more of *P. fluorescens* NRRL B-50851, *P. fluorescens* NRRL B-50852, and *P. fluorescens* NRRL B-50853, alone or with an agriculturally acceptable carrier. Further, the biocontrol agents of this invention can contain one or more of the bacteria, an agriculturally acceptable carrier, and at least one herbicide and/or at least one fertilizer (see Table 3 for a non-limiting list of herbicides and fertilizers that can be in the compositions of this invention).

The biocontrol agents of this invention contain sufficient amounts of one or more of *P. fluorescens* NRRL B-50851, *P. fluorescens* NRRL B-50852, and *P. fluorescens* NRRL B-50853 described herein to control the growth of *P. annua* L. and/or *P. trivialis*. The concentration of each *P. fluorescens* in the biocontrol agents of this invention is at least $10^4$ colony forming units (cfu) per unit of composition. In another embodiment, the concentration of each *P. fluorescens* in the biocontrol agents can range from approximately $10^5$ to approximately $10^{11}$ cfu per unit of composition. In another embodiment, the concentration of each *P. fluorescens* in the biocontrol agents can range from approximately $10^6$ to approximately $10^{10}$ cfu per unit of composition. In yet another embodiment, the concentration of each *P. fluorescens* in the biocontrol agents can range from approximately $10^7$ to approximately $10^9$ cfu per unit of composition. In another embodiment, the concentration of each *P. fluorescens* in the biocontrol agents of this invention is $10^8$ cfu per unit of composition.

When two or more of the bacterial strains of this invention are combined in a biocontrol agent, or applied sequentially or together, the results are often better than when a single bacterial strain is used alone. This result is surprising and unexpected. Thus, one is able to apply a smaller amount of each bacterial strain per unit area when two or more strains are used, than when only one bacterial strain is applied. So, when any two of *P. fluorescens* NRRL B-50851, *P. fluorescens* NRRL B-50852, and *P. fluorescens* NRRL B-50853, or when all three bacterium are combined in a biocontrol agent or applied sequentially or together, the concentration of each bacterial strain can range from approximately $10^6$ to approximately $10^9$ cfu per unit of composition. In another embodiment, the concentration of each *P. fluorescens* in a biocontrol agent containing two or three of these bacteria can be approximately $10^7$ cfu per unit of composition. When applying two or three strains of these bacteria to a unit area, the concentration of each bacterial strains applied can range from approximately $10^6$ to approximately $10^9$ cfu per unit area, or from approximately $10^7$ to approximately $10^8$ cfu per unit area, or approximately $10^7$ cfu per unit area.

As used herein, the term “agriculturally acceptable carrier” includes any liquid or solid carrier to which the bacteria of the present invention can be added and that is not harmful to the bacteria of the invention or the plants to which it is being applied. An agriculturally acceptable carrier is any liquid or solid that can be combined with the *P. fluorescens* of this invention and that assists in the application of the *P. fluorescens* strains of this invention to the soil so that the *P. fluorescens* strains of this invention grow and colonize the soil and roots of *Poa annua* L and/or *Poa trivialis*. Non-limiting examples of agriculturally acceptable carriers include talc, starch, sucrose, lactose, and other carbohydrates, polysaccharides, milk/skim milk, cellulose, water, a buffered solution, methylcellulose, clay, sand, peat, vermiculite, diatomaceous earth, a cereal grain flour or meal, cotton meal, rice, seeds, and liquid media. A carrier can also be a polymeric porous material, such as polyvinyl alcohol (PVA), polyethylene glycol (PEG), polyacrylic acid (PAA), poly(lactic acid) (PLA), poly (glycolic acid) (PGA), copolymer of poly(lactic-co-glycolic acid) (PLGA), poly(ϵ-caprolactic acid) (PCLA), poly(β-hydroxybutyric acid), poly(β-hydroxyvaleric acid), polydioxanone, poly(ethylene oxide), poly(malic acid), poly(tartronic acid), polyphosphazene, polyethylene (PE), polystyrene (PS), agar (alginate) or other polysaccharides, gelatin, or combinations thereof. The carrier should not kill the bacteria of the invention. Also the carrier should release the bacteria of the invention into the soil after application to the soil or onto plants after application onto the plants. Such release of the bacteria may occur after a period of rain or irrigation or other type of application of water to the soil and/or plant. Any carrier that permits the bacteria of the present invention to be delivered to the soil and/or target plant in a manner such that the bacteria remains viable may be employed in the composition so long as the carrier does not harm turfgrasses, native plants, and crops.

A dry formulation of the bacteria of the present invention can be produced by several drying methods including freeze drying, air drying, spray drying, or fluidized bed drying. Skim milk, sucrose, lactose, dextran, etc., can be added to the bacteria to act as both protectants during the drying process and as carriers.

In one embodiment, one or more of *P. fluorescens* NRRL B-50851, *P. fluorescens* NRRL B-50852, and *P. fluorescens* NRRL B-50853 can be combined with a cereal grain flour or meal and formed into pellets. For example, liquid media containing approximately $10^8$ of *P. fluorescens* NRRL B-50851, *P. fluorescens* NRRL B-50852, or *P. fluorescens* NRRL B-50853 is freeze-dried using known in the art methods. The freeze-dried media is then mixed with a cereal grain flour and water and passed through an extruder so that spherical pellets or cylindrical pellets are made, and allowed to dry.

One can then spread the pellets onto the soil and/or plants in the area to be treated when the ground is moist, or prior to rain being expected to occur, or prior to irrigating the area. When wet, the a cereal grain flour pellets decay and provide food for the *P. fluorescens* NRRL B-50851, *P. fluorescens* NRRL B-50852, or *P. fluorescens* NRRL B-50853. In an alternative embodiment, if one intends to use two or three of *P. fluorescens* NRRL B-50851, *P. fluorescens* NRRL B-50852, and/or *P. fluorescens* NRRL B-50853, then liquid media containing approximately $10^7$ of each bacteria are sprayed-dried, and then are mixed with the a cereal grain flour and water, are extruded into the desired shape, and are allowed to dried. Optional pellet shapes can include, but are not limited to conical, cube, cuboid, prism (hexagonal or other shape), tetrahedron, octahedron, and dodecahedron. The pellets can range in size from approximately 1 mm³ to approximately 10 cm³; or from approximately 10 mm³ to approximately 5 cm³, or from approximately 20 mm³ to approximately 1 cm³. Depending on the pellet's shape and the mode of spreading, one may want to smooth the pellet's edges to improve the spreading of the pellets. One can broadcast spread pellets or aerial spray pellets.

In an alternative embodiment, one can freeze-dry the media containing approximately $10^8$ of *P. fluorescens* NRRL B-50851, *P. fluorescens* NRRL B-50852, or *P. fluorescens* NRRL B-50853, or a combination thereof at a concentration of approximately $10^7$ of bacteria with talc. Then one can mix the talc containing the bacteria with seeds of desired plants. The talc/bacteria combination sticks to the seeds. Then one can spread the bacteria-coated seed of the desired plant.

Alternatively, one can mix a herbicide or fertilizer or both with one or more of the bacteria (in liquid media or previously dried via spray-drying or freeze-drying; optionally previously combined with a carrier), optionally combine with a carrier, and apply the mixture onto the soil or plants in the area desired to be treated.

Not wishing to be bound to any particular theory, it is believed that during colonization of *P. annua* L. and *P. trivialis* roots, the *P. fluorescens* strains of this invention occupy the intracellular spaces of the weeds' roots and produce one or more inhibitory compounds that suppress root elongation of the weeds. Not wishing to be bound to any particular hypothesis, it is believed that the bacteria inhibit lipopolysaccharide production in the cell wall and cell membrane in the root leading to the lack of root elongation especially during the cool seasons from fall to early spring. A similar mechanism of action occurs for the bacteria of this invention with *P. trivialis*. The basis for this hypothesis is that *P. fluorescens* strain D7 demonstrates this mechanism of action with downy brome. See Gurusiddaiah, et al., 1994 *Weed Science* 42(3): 492-501. Thus, to be effective, *P. fluorescens* NRRL B-50851, *P. fluorescens* NRRL B-50852, and/or *P. fluorescens* NRRL B-50853 should reside in close proximity to the root cells of annual bluegrass or rough bluegrass. The lack of root growth of *Poa annua* L. and *P. trivialis* during the fall, winter, and spring (during time the plants actively grow) reduces the competitive ability of these weeds and allows the desirable turfgrasses to flourish. The bacteria can be successful in all environments where *Poa annua* L. or *P. trivialis* grows, especially those areas with cool or cold winters. Thus, application of the biocontrol agents of this invention (the bacteria of this invention and compositions containing the bacteria) are useful to control root growth of the embryo or seedling of annual bluegrass and/or rough bluegrass.

*P. fluorescens* NRRL B-50851, *P. fluorescens* NRRL B-50852, and *P. fluorescens* NRRL B-50853 grow and are metabolically active during conditions that *P. annua* L. and *P. trivialis* are actively growing roots, at cooler air temperatures (e.g., between approximately 32° F. and approximately 60° F.) and when the soil has high moisture content. When the air temperature is too warm and/or when the soil is too dry, both the bacteria of this invention and *P. annua* L. and *P. trivialis* go dormant. When dormant, the polysaccharide coating of *P. fluorescens* NRRL B-50851, *P. fluorescens* NRRL B-50852, and *P. fluorescens* NRRL B-50853 protect the bacteria from the harsh environmental conditions. In one embodiment, application of the biocontrol agents described herein (the bacteria and/or compositions containing the bacteria) to the soil occurs in fall when air temperatures are below 50° F. and rain is predicted or irrigation is intended shortly after application. In another embodiment, application of the biocontrol agents described herein to the soil when air temperatures range from approximately 32° F. to 80° F.; or approximately 35° F. to approximately 60° F.; or approximately 35° F. to approximately 55° F. Application occurs when the ground has sufficient moisture or when rain is predicted or prior to irrigating the land. Alternatively, one could have irrigated the land prior to application of the biocontrol agents of this invention. Alternatively, one applies an inhibitory amount of the biocontrol agents described herein with or to turf and/or turfgrass seed. Application can occur to soil that is bare of plants, to field of dormant weeds, to a field of actively growing weeds, to a field with dormant turfgrass, or to a field of actively growing turfgrasses. In general, one applies an effective inhibitory amount of the biocontrol agentsto the soil surface or soil subsurface in an area where one wants to or is growing turfgrass or small grain crop area.

The types of desirable crops and/or turfgrasses that the *P. fluorescens* strains do not inhibit are listed in Table 4, infra. Testing included all economically important plant species of the area, and those plants known to be involved in ecosystem maintenance. In agronomic ecosystems, the major crop species are of interest. The U.S. Environmental Protection Agency (EPA) published a list of the top 25 major agricultural crops. These plants were placed on this list because of their economic importance, ecosystem activity or total production values (EPA, 2011).

One can spray the biocontrol agents onto the bare soil or onto a field of turfgrass. In one embodiment, spraying is performed after a rain or irrigation (when the soil is moist). In another embodiment, spraying is performed shortly before rain is anticipated and/or during periods of high rain probability, and/or prior to irrigating the area of application. Application of the bacteria in liquid or suspension form and/or the compositions of this invention may be accomplished by ground or aerial spraying using equipment routine to one of skill in the art. The nozzle of the sprayer may be adjusted for size by one of skill in the art to accommodate the size of the area being treated and any plants in that area, as well as the type and size of presently disclosed carriers.

One can apply the bacteria of this invention or compositions of this invention onto seed as a seed coating and then drill the seed into the soil or broadcast the seed. In one embodiment, the seed coated with the bacterium of this invention or compositions of this invention can be drilled or broadcast in the fall of the year into moisture, and the desired seed will spread the bacterium throughout the soil. In another embodiment, the bacteria-coated seed can be drilled or broadcast at any time prior to rain or application of water (irrigate) to the area where the coated seed are drilled or broadcasted. For example, to make a biocontrol agent containing a seed coated with one or more of the bacteria described herein, one grows one or more of the species of bacteria to approximately $10^8$ cells/L, and then one can apply the bacteria to the seed by making a slurry of approximately 10 oz. media per approximately 60 pounds seed and rotate the slurry in a drum. After the seeds are dry, one can direct drill or broadcast the biocontrol agent (bacterial-coated seed) at recommended seeding rates, which for wheat seed is approximately 60 pounds per acre. If one has freeze-dried media containing approximately $10^8$ cells/L, then one can apply the bacteria to the seed by making a slurry of approximately 2 g freeze-dried bacteria with approximately 60 pounds per acre of seed and rotate the slurry in a drum. After the seeds are dry, one can direct drill or broadcast seed at recommended seeding rates, which for wheat seed is approximately 60 pounds per acre. For liquid spraying, one can use approximately 4 gallons of liquid media containing $10^8$ cells bacteria per L per acre of land being treated or 2 g of freeze-dried media/cells per acre. For 20 acres, apply approximately 80 gallons of liquid per acre or approximately 40 g in 50 to 1000 gallons. Final minimum concentration can be approximately 10 million cells per square foot soil surface. The liquid spray can be applied by back pack sprayer, ground sprayer or aerially applied.

Individual strains of bacteria can be cultured by standard methods using well-known in the art techniques for a sufficient amount of time (in one embodiment, approximately 32 hours) such that sufficient bacteria grow.

The "root system" of a plant includes the rhizoplane (root surface) and the rhizosphere (soil immediately surrounding the roots).

One can have a kit containing one or more of the *P. fluorescens* described herein for controlling the growth of annual bluegrass and/or rough bluegrass. A kit may contain one or more containers, each having one or more of the *P. fluorescens* described herein, in a liquid or dry formulation, and written instructions for using the kit to control the growth of annual bluegrass and/or rough bluegrass. Alternatively, the kit may contain seeds or other agriculturally acceptable carriers that contain the *P. fluorescens* described herein. The kit may optionally contain one or more herbicides and/or fertilizer that can be applied with the bacteria. As discussed supra, the concentration of the *P. fluorescens* within the kit can depend on the number of the bacteria contained within the kit. For example if only one of the *P. fluorescens* described herein is contained within the kit, the concentration of the bacterium may be approximately $10^8$ per area for treatment. Alternatively, if two of the *P. fluorescens* described herein are within the kit, the concentration for each bacterium may be only approximately $10^7$ per area for treatment. Further, if all three of the bacteria described herein are contained in the kit, then the concentration for each bacterium may be only approximately $10^6$ per area for treatment.

The terms "approximately" and "about" refers to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Example 1

Isolating Bacteria with Inhibitory Growth Activity

To reduce the growth of annual bluegrass, a bacterial strain has the ability to establish and grow in the microhabitat where it is to be used. The bacteria has the ability to colonize the root system of annual bluegrass. Therefore, bacteria are selected by isolating bacteria from the rhizoplane, the rhizosphere, or both rhizoplane and rhizosphere of annual bluegrass and turfgrasses. In addition the bacteria are able to selectively inhibit *Poa annua* L. and not hurt the desirable plants, which are desirable turfgrass, crops, and native plants.

The method for isolating the bacteria that can control of *P. annua* L. and *P. trivialis* is illustrated in FIG. 1. A general description of this isolation method follows. Turfgrass or annual bluegrass are dug from the field and adhering soil is gently washed from the roots with flowing tap water. The roots are excised from the shoots. The bacteria are collected and isolated by placing the excised roots in sterile water and shaking the mixture vigorously to remove organisms clinging to the root surface. Then serial dilutions are prepared and spread plated on SR agar (see Sands and Rovira, 1970. *Applied Microbiology* 20:513-514). The plates are then incubated 20° C. Each isolate growing on the plates after 32 hours is then removed and streaked for isolation onto a new Petri plate containing SR agar. Single colony isolates are then placed into long-term storage until further testing is performed.

For long-term storage during the screening procedure, inoculum from individual colonies is grown in SR broth, centrifuged at room temperature (4,000 rpm for 10 minutes). The supernatant is decanted, and the pellet is resuspended in 1 mL of fresh sterile SR broth. This solution is mixed with sterile glycerol (1:1) in a two mL cryovial (VWR International, Radnor, Pa.) and stored in −80° C. ultra-low freezer (Labconco, Kansas City, Mo.).

Example 2

In-Vitro Screening Isolated Bacterial Strains

Bacteria colonies isolated in Example 1 are screened to select for bacteria strains that inhibit annual bluegrass growth in-vitro as exhibited by reduction in root growth or germination as compared to control plants. The bacteria strains inhibitory to annual bluegrass are then tested against various turfgrass species and other economically important plants. The bacteria strains that do not deleteriously affect turfgrass growth in-vitro are selected for further study.

TABLE 4

Suppression of root growth of various plant species in agar bioassays investigating *Pseudomonas fluorescens* strains XJ3, XS18, or LRS12.

| Common Name | Latin Name | XJ3 | XS18 | LRS12 |
|---|---|---|---|---|
| | | Root Growth Bioassay % Suppression | | |
| MONCOTYLEDONS | | | | |
| Annual bluegrass | *Poa annua* | 100 | 98 | 94 |
| Bahiagrass | *Paspalum notatum* | 0 | 10 | 0 |
| Barley | *Hordeum vulgare* L. | 0 | 0 | 0 |
| Basin wildrye | *Elymus linareus* | 0 | 0 | 0 |
| Bentgrass - Creeping | *Agrostis palustris* | 0 | 0 | 0 |
| Bermudagrass | *Cynodon dactylon* | 0 | 0 | 0 |
| Birdseye bluegrama | *Bouteloua gracilis* | 0 | 0 | 0 |
| Bluebunch wheatgrass | *Agropyron spicatum* | 20 | 0 | 0 |
| Bluegrass - Kentucky | *Poa pratensis* | 0 | 0 | 0 |
| Bottlebrush squirreltail | *Elymus elymoides* | 0 | 0 | 0 |
| Buffalograss | *Buchloe dactyloides* | 0 | 0 | 0 |
| Carpetgrass | *Axonopus fissifolius* | 0 | 0 | 0 |
| Cody buffalograss | *Buchloe dactyloides* | 0 | 0 | 0 |
| Columbia needlegrass | *Stipa columbian* | 0 | 0 | 0 |
| Corn | *Zea mays* L. | 0 | 0 | 0 |
| *Dichrondra* | *Dichondra micrantha* | 0 | 0 | 0 |

TABLE 4-continued Suppression of root growth of various plant species in agar bioassays investigating *Pseudomonas fluorescens* strains XJ3, XS18, or LRS12.

| Common Name | Latin Name | XJ3 | XS18 | LRS12 |
|---|---|---|---|---|
| | | \multicolumn{3}{c}{Root Growth Bioassay % Suppression} | | |
| Downy brome | *Bromus tectorum* L. | 0 | 30 | 10 |
| Eastern Gamagrass | *Tripsacum dactyloides* | 0 | 0 | 0 |
| Fescue - Creeping Red | *Festuca rubra* var. *rubra* | 10 | 0 | 0 |
| Fescue - Tall | *Festuca arundinacea* | 10 | 0 | 0 |
| Idaho fescue | *Festuca idahoensis* | 0 | 0 | 0 |
| Kikuyugrass | *Pennisetum clandestinum* | 0 | 0 | 0 |
| Orchardgrass | *Dactylis glomerata* | 0 | 0 | 0 |
| Ryegrass - Perennial | *Lolium perenne* | 0 | 0 | 0 |
| Saint Augustine grass | *Stenotaphrum secundatum* | 0 | 0 | 0 |
| Smooth bromegrass | *Bromus inermis* | 20 | 0 | 0 |
| Wheatgrass - Bluebunch | *Agropyron spicatum* | 10 | 10 | 20 |
| Wheatgrass - Crested | *Agropyron cristatum* | 10 | 0 | 0 |
| Zoysiagrass - *Japonica* | *Zoysia japonica* | 10 | 20 | 0 |
| DICOTYLEDONS | | | | |
| Alfalfa | *Medicago sativa* L. | 0 | 0 | 0 |
| Apple | *Malus* Mill. | 0 | 0 | 0 |
| Beans | *Phaseolus* L. | 0 | 0 | 0 |
| Big sagebrush | *Artemisia tridentata* | 0 | 0 | 0 |
| Camelina | *Camelina sativa* L. | 0 | 0 | 0 |
| Canola | *Brassica napus* L. | 0 | 0 | 0 |
| Celery | *Apium* spp. L. | 0 | 0 | 0 |
| Chick peas | *Cicer arietinum* | 0 | 0 | 0 |
| Clover | *Trifolium* L. | 0 | 0 | 0 |
| Common vetch | *Vicia sativa* L. | 0 | 0 | 0 |
| Cucumber | *Cucumis sativus* L. | 0 | 0 | 0 |
| Faba bean | *Vicia faba* | 0 | 0 | 0 |
| Flax | *Linum narbonense* L. | 0 | 0 | 0 |
| Jointvetch | *Aeschynomene* sp. L. | 0 | 0 | 0 |
| Lentil | *Lens culinaris* Medik. | 0 | 0 | 0 |
| Lettuce | *Lactuca sativa* L. | 0 | 0 | 0 |
| Mint | *Mentha* L. | 0 | 0 | 0 |
| Northern bedstraw | *Galium boreale* L. | 0 | 0 | 0 |
| Pea | *Pisum sativum* L. | 0 | 0 | 0 |
| Peanuts | *Arachis* L. | 0 | 0 | 0 |
| Pepper | *Capsicum* L. | 0 | 0 | 0 |
| Phlox | *Phlox* L. | 0 | 0 | 0 |
| Potato | *Solanum* | 0 | 0 | 0 |
| Rannucula | *Ranunculus* | 0 | 0 | 0 |
| Rapeseed | *Brassica rapa* L. | 0 | 0 | 0 |
| Safflower | *Carthamus tinctorius* L. | 0 | 0 | 0 |
| Soybeans | *Glycine max* L. Merr. | 0 | 0 | 0 |
| Squash | *Cucurbita* spp. | 0 | 0 | 0 |
| Sugar beets | *Beta vulgaris* | 0 | 0 | 0 |
| Sunflower | *Helianthus* L. | 0 | 0 | 0 |
| Tomato | *Solanum* | 0 | 0 | 0 |
| Vetch | *Vicia* spp. | 0 | 0 | 0 |

Individual bacteria colonies are inoculated into *Pseudomonas* minimal salts medium (PMS) described by Gasson, *Applied and Environmental Microbiology* 39:25-29 (1980), and grown at 20° C. (68° F.) for 32 hours until late logarithmic growth (about $10^9$ to $10^{11}$ cfu/mL culture medium).

Annual bluegrass growth inhibition is assessed by a seed germination and root elongation assay. Briefly, one mL of test bacterial cultures is added to water agar plates. The water agar plates consist of 18 mL of 0.9% sterile, molten agar (50° C.) added to a Petri plate and allowed to solidify. Twenty annual blue grass seed are added to the bacterial dishes, as well as to control dishes with no bacteria, and allowed to grow at 15° C. After five days, plant root length is measured. The test bacteria inhibit the annual bluegrass if root lengths of the seedling treated with the bacteria are more than 20 percent less than the control root lengths. This procedure is the first step in determining those isolates to study further. Two plates are prepared for each organism tested. Control plates are prepared by using the non-inoculated growth medium instead of the bacteria cell culture. The plates are slanted slightly so the roots grow down and through the agar. Before root growth from the seedlings interferes with each other, in about 5 days, the seedlings are pulled from the agar, and root length and germination are recorded. The bacteria showing significant inhibition of annual bluegrass root length or lack of germination when compared to the control seeds are then tested against desirable turfgrass, crop and native seedling growth (infra). Significant inhibition of annual bluegrass in the in-vitro test is defined as at least a 50% reduction in root length when compared to the control or at least a 20% reduction in germination when compared to the control.

Over 20,000 bacteria were isolated from soil in Example 1. Half of these or 10,000 bacteria have some inhibitory effect on annual bluegrass and desirable plants in water agar seed root length inhibition and germination assays as tested in Example 2. Yet, approximately 200 bacterial isolates had some inhibitory effect to annual bluegrass seedlings, but did not inhibit grow of turfgrass seedlings. These approximately 200 bacterial isolates are then tested for sustained and sufficient inhibitory effect against annual bluegrass when applied to soil in pots grown in the growth chamber. Table 4, above, provides the results for *Pseudomonas fluorescens* strains XJ3, XS18, and LRS12.

Example 3

Screening Bacterial Strains in the Growth Chamber

Bacterial strains showing significant inhibition of annual bluegrass root length or germination in Example 2 (supra) are subjected to a first screening in soil by separately growing annual bluegrass plants and turfgrass species in a growth chamber or greenhouse in the presence of the bacterial strain. Those bacteria strains are selected that inhibit annual bluegrass without deleteriously affecting desirable turfgrass.

Ritzville silt loam is obtained from a site in Lind, Wash. and passed through a 4 mm screen and then a 2 mm screen to obtain a uniform soil mixture. The screened silt loam is amended with 20% sand by weight and is used as soil in the pots. Pots are filled with soil and seeded with annual bluegrass or with turfgrass seeds. 6.4 cm diameter by 7.6 cm deep plastic pots seeded with 6-9 annual bluegrass seeds and 7.6 cm diameter by 15.2 cm deep plastic pots seeded with 5 turfgrass seeds are convenient sizes for growth chamber or greenhouse studies.

The amount of bacteria per annual bluegrass seed in the test pots is selected to optimize the selection of field-effective strains and to minimize the selection of field-ineffective strains. In particular, $10^7$ cfu of the test strain per annual bluegrass test pot is applied to the soil surface. A rate of $10^7$ cfu bacteria are applied per pot in 5 mL of water by dropping the material onto the surface of the soil. Four turfgrass seeds are planted on the surface of the pot and covered with sand to assess the effect of the bacteria on turfgrass seeds and seedlings in natural, non-autoclaved soil. Separate annual bluegrass and turfgrass seed controls are prepared identical to the test samples except without bacterial treatment as controls.

The soil is wetted to provide good plant growth, and the pots incubated in the growth chamber with 14-hour day at 18° C. and a 10-hour night at 13° C. After approximately 3 weeks to approximately 4 weeks, the plants and soil are removed from the pots; annual bluegrass and turfgrass seedlings and their roots are washed with water until free of soil. The roots and shoots of the annual bluegrass and turfgrass seedlings are excised, and are dried at 60° C. for 48 hours to remove water so that a comparison to the control plants can be made.

To evaluate the bacterial treatment, root and shoot dry weight of the annual bluegrass plants and turfgrass seedlings are compared with the root and shoot dry weight of the control annual bluegrass and turfgrass seedlings. Bacterial strains that cause the treated annual bluegrass seedlings to have reduced root growth (root dry weight), as compared to the control group root growth (root dry weight), of at least 30% or that cause the treated annual bluegrass seedlings to have reduced shoot growth (shoot dry weight), as compared to the control group shoot growth (shoot dry weight), of at least 30% are considered inhibitory to annual bluegrass.

Of the less than 200 bacterial strains that may inhibit root growth of annual bluegrass, but not inhibit root growth of economically important crops or turfgrasses in the water agar bioassay, ten bacterial strains are found to inhibit growth of annual bluegrass but not turfgrass when applied to natural soils in pots and grown in the greenhouse. Upon further testing of the 10 isolates, it is discovered that four isolates are inconsistent in producing the compound(s) that inhibit root elongation as evident by inconsistent inhibition of root elongation. The production of anti-microbial activity disqualified another three strains from further study. The results for *Pseudomonas fluorescens* strains XJ3, XS18, or LRS12 are presented in Table 5 below. Only three bacterial isolates are chosen for field studies; *Pseudomonas fluorescens* strains XJ3, XS18, and LRS12.

TABLE 5

Suppression of various plant species grown in natural, non-autoclaved soil in growth chambers after application of three Pseudomonas fluorescens strains: either XJ3, XS18, or LRS12.

| Common Name | Latin Name | XJ3 | XS18 | LRS12 |
|---|---|---|---|---|
| | | Plant Growth in Soil/ Growth Chamber % Suppression | | |
| MONCOTYLEDONS | | | | |
| Annual bluegrass | *Poa annua* | 96 | 97 | 91 |
| Bahiagrass | *Paspalum notatum* | 0 | 0 | 0 |
| Barley | *Hordeum vulgare* L. | 0 | 0 | 0 |
| Basin wildrye | *Elymus linareus* | 0 | 0 | 0 |
| Bentgrass - Creeping | *Agrostis palustris* | 0 | 0 | 0 |
| Bermudagrass | *Cynodon dactylon* | 0 | 0 | 0 |
| Birdseye bluegrama | *Bouteloua gracilis* | 0 | 0 | 0 |
| Bluebunch wheatgrass | *Agropyron spicatum* | 0 | 0 | 0 |
| Bluegrass - Kentucky | *Poa pratensis* | 0 | 0 | 0 |
| Bottlebrush squirreltail | *Elymus elymoides* | 0 | 0 | 0 |
| Buffalograss | *Buchloe dactyloides* | 0 | 0 | 0 |
| Carpetgrass | *Axonopus fissifolius* | 0 | 0 | 0 |
| Cody buffalograss | *Buchloe dactyloides* | 0 | 0 | 0 |
| Columbia needlegrass | *Stipa columbian* | 0 | 0 | 0 |
| Corn | *Zea mays* L. | 0 | 0 | 0 |
| Dichrondra | *Dichondra micrantha* | 0 | 0 | 0 |
| Downy brome | *Bromus tectorum* L. | 0 | 10 | 0 |
| Eastern Gamagrass | *Tripsacum dactyloides* | 0 | 0 | 0 |
| Fescue - Creeping Red | *Festuca rubra* var. *rubra* | 0 | 0 | 0 |
| Fescue - Tall | *Festuca arundinacea* | 0 | 0 | 0 |
| Idaho fescue | *Festuca idahoensis* | 0 | 0 | 0 |
| Kikuyugrass | *Pennisetum clandestinum* | 0 | 0 | 0 |
| Orchardgrass | *Dactylis glomerata* | 0 | 0 | 0 |
| Ryegrass - Perennial | *Lolium perenne* | 0 | 0 | 0 |
| Saint Augustine grass | *Stenotaphrum secundatum* | 0 | 0 | 0 |
| Smooth bromegrass | *Bromus inermis* | 0 | 0 | 0 |
| Wheatgrass - Bluebunch | *Agropyron spicatum* | 0 | 0 | 0 |

TABLE 5-continued

Suppression of various plant species grown in natural, non-autoclaved soil in growth chambers after application of three Pseudomonas fluorescens strains: either XJ3, XS18, or LRS12.

| Common Name | Latin Name | XJ3 | XS18 | LRS12 |
|---|---|---|---|---|
| | | Plant Growth in Soil/ Growth Chamber % Suppression | | |
| Wheatgrass - Crested | *Agropyron cristatum* | 0 | 0 | 0 |
| Zoysiagrass - *Japonica* | *Zoysia japonica* | 0 | 0 | 0 |
| DICOTYLEDONS | | | | |
| Alfalfa | *Medicago sativa* L. | 0 | 0 | 0 |
| Apple | *Malus* Mill. | 0 | 0 | 0 |
| Beans | *Phaseolus* L. | 0 | 0 | 0 |
| Big sagebrush | *Artemisia tridentata* | 0 | 0 | 0 |
| Camelina | *Camelina sativa* L. | 0 | 0 | 0 |
| Canola | *Brassica napus* L. | 0 | 0 | 0 |
| Celery | *Apium* spp. L. | 0 | 0 | 0 |
| Chick peas | *Cicer arietinum* | 0 | 0 | 0 |
| Clover | *Trifolium* L. | 0 | 0 | 0 |
| Common vetch | *Vicia sativa* L. | 0 | 0 | 0 |
| Cucumber | *Cucumis sativus* L. | 0 | 0 | 0 |
| Faba bean | *Vicia faba* | 0 | 0 | 0 |
| Flax | *Linum narbonense* L. | 0 | 0 | 0 |
| Jointvetch | *Aeschynomene* sp. L. | 0 | 0 | 0 |
| Lentil | *Lens culinaris* Medik. | 0 | 0 | 0 |
| Lettuce | *Lactuca sativa* L. | 0 | 0 | 0 |
| Mint | *Mentha* L. | 0 | 0 | 0 |
| Northern bedstraw | *Galium boreale* L. | 0 | 0 | 0 |
| Pea | *Pisum sativum* L. | 0 | 0 | 0 |
| Peanuts | *Arachis* L. | 0 | 0 | 0 |
| Pepper | *Capsicum* L. | 0 | 0 | 0 |
| Phlox | *Phlox* L. | 0 | 0 | 0 |
| Potato | *Solanum* | 0 | 0 | 0 |
| Rannucula | *Ranunculus* | 0 | 0 | 0 |
| Rapeseed | *Brassica rapa* L. | 0 | 0 | 0 |
| Safflower | *Carthamus tinctorius* L. | 0 | 0 | 0 |
| Soybeans | *Glycine max* L. Merr. | 0 | 0 | 0 |
| Squash | *Cucurbita* spp. | 0 | 0 | 0 |
| Sugar beets | *Beta vulgaris* | 0 | 0 | 0 |
| Sunflower | *Helianthus* L. | 0 | 0 | 0 |
| Tomato | *Solanum* | 0 | 0 | 0 |
| Vetch | *Vicia* spp. | 0 | 0 | 0 |

To evaluate the bacterial treatment on economically important turfgrass species, on economically important crop plants and on desirable native plant species, root and shoot dry weight of the plants treated with the bacteria are compared with root and shoot dry weight of the control plants with no bacterial treatment. Any bacterium that did not deleteriously affect the treated turfgrass or for which the turfgrass plants had less than approximately 10% reduction in root growth (root dry weight) or shoot growth (shoot dry weight) compared to the control plants, or that caused at least approximately 30% reduction in annual bluegrass shoot dry weight and/or root dry weight, are considered being acceptable for testing in the next stage of testing in field plots. See Table 5 for the results for *Pseudomonas fluorescens* strains XJ3, XS18, or LRS12.

Example 4

Screening Bacterial Strains in the Test Plots

For the field test, annual bluegrass plants are grown in plots that are substantially free of other weeds so that variability resulting from the presence of other weeds is reduced. Field test plots (treatment plots) are approximately 2 meters to approximately 3 meters wide by approximately 9 meters long. Negative control plots are within about 6 meters of the treatment plot so that the treatment plot and non-treatment plot (negative control plot) have similar soil conditions. A plot can range in size from approximately 10 m² to approximately 50 m².

The plots seeded with annual bluegrass have about 50 seeds m⁻² to about 75 seeds m⁻². Individual bacterial strains (identified in Example 3 supra) are applied once to the soil as a spray treatment. The spray treatment can be applied at any time between seeding to 4 weeks after seeding. The bacteria are applied to moist soil to help insure survival of the microorganisms. For the spray treatment, each test bacteria, contained in distilled water, are sprayed on to the soil to provide a concentration of about 10⁷ cfu to about 10⁸ cfu of the bacteria m⁻². Negative control plots of annual bluegrass are treated identical to the test plot of annual bluegrass except that no bacteria are applied. To have statistical significance, each microorganism treatment is replicated a minimum of three times.

Plots seeded with turfgrass (about 100 seeds m⁻² to about 150 seeds m⁻²) are seeded beside or with the annual bluegrass plots. The bacteria mixed with distilled water are sprayed on the test plots' soil to provide a concentration of about 10⁸ cfu of the bacteria m⁻². The treatment is applied to moist soil at any time between seeding to 4 weeks after seeding. The negative control plots of turfgrass seed are treated identical to the test plot of turfgrass seed except that no bacteria are applied. To have statistical significance, each microorganism treatment is replicated a minimum of three times.

To assess the effect of the bacterial treatment on the inhibition of annual bluegrass in the field, after adequate growth has occurred (e.g., about the 3- to 5-leaf-stage), at least one of the following is obtained: root dry weight, shoot dry weight, or stand (numbers of plant m⁻²). Root dry weight and shoot dry weight are obtained as described in Example 3 (supra). Bacterial strains that cause the treated annual bluegrass plants to average a reduction in root growth (root dry weight), reduction in shoot growth (shoot dry weight), or reduction in stand (numbers of plant m⁻²) of at least 20% when compared to negative control annual bluegrass plants are considered inhibitory to annual bluegrass in the field test. To assess the effect of the bacterial treatment on turfgrass, at least one of the following is obtained: root dry weight, shoot dry weight, or stand. Root dry weight and shoot dry weight are obtained as described in Example 3 (supra). Those bacterial strains that cause turfgrass to average less than 10% reduction in root growth (root dry weight) or shoot growth (shoot dry weight) or stand (numbers of plant m⁻²) compared to negative control crop plant plots are defined as not deleteriously affecting the crop plants.

Of the approximately 200 bacteria isolates tested for inhibitory effect against annual bluegrass in the test field in this Example 4, only 20 bacteria isolates (0.1% of the original number of bacteria isolated) have inhibitory effect on annual bluegrass and no deleterious effect on turfgrass.

Example 5

Field Testing

The twenty most promising bacteria strains from the growth chamber test and the field test (Examples 3, 4, respectively) are then tested in the field near Pullman, Wash. *Poa annua* L. seeds collected from Pullman are planted by hand in furrows. Because *Poa annua* L. seeds are small, the seeds are mixed with sterile sand and then scattered in the row to obtain a seeding of approximately one seed per inch. Winter wheat cultivar 'Madsen' is also planted in rows at approximately one seed per inch. Each bacterial inoculum is applied directly to seeds in the furrow at 20 mL/m to obtain a concentration of approximately 10⁸ cfu per m² that is sufficient to obtain root colonization and plant inhibition. (Kennedy, A. C., et al. 1991. Rhizobacteria suppressive to the weed downy brome. *Soil Sci. Soc. Amer. J.* 55:722-727.) Control plots having the same concentration of annual bluegrass seeds or winter wheat cultivar 'Madsen' seeds are treated with 20 mL of sterile deionized water. The average annual precipitation at Pullman is 450-600 mm, and the soil is a Palouse silt loam. Rows are 1 m long with 0.30 m between each row. Of the twenty strains of bacteria that had favorable results in Example 4 above, eleven strains had unfavorable results in this field test.

Of the nine bacterial strains with favorable results, three bacterial strains, *P. fluorescens* XS18 (NRRL B-50852), *P. fluorescens* XJ3 (NRRL B-50851), and *P. fluorescens* LRS12 (NRRL B-50853) (2013 only) are subjected to additional testing. These three strains are randomly applied to half of the rows in the fall of each year. In early April 2012 or August 2013, *Poa annua* L. plants in 7 rows are counted to obtain plot stands. The above-ground shoot mass and below ground root mass of *Poa annua* L. and winter wheat cultivar 'Madsen' are determined using the methods described supra. Bacterial strains are considered inhibitory to *Poa annua* L. in this field test if *Poa annua* L. in the plots treated with the bacteria averaged at least a 20% reduction in stand (numbers of plant m⁻²); root growth (root dry weight of 0.25 m³ of soil); and shoot growth (shoot dry weight per 0.25 m²) when compared to control plots. Bacterial strains that caused less than a 10% reduction in Kentucky bluegrass stand (numbers of plant m⁻²); root growth (root dry weight of 0.25 m³ of soil); and shoot growth (shoot dry weight per 0.25 m²) compared to control winter wheat are considered as not injurious to the crop.

All three bacteria strains tested in the field inhibit *Poa annua* L. root growth more than 39% (Table 6). *P. fluorescens* strain XS18, applied to the furrow in which *Poa annua* L. seed was planted in the fall of 2011, inhibit shoot mass by 44% and root mass by 74% at harvest in June of 2012. *P. fluorescens* strain XS18 also inhibit *Poa annua* L. shoot mass by 78% and root mass by 79% when the bacteria are applied to seed in the fall of 2012 and harvested in August of 2013. When *P. fluorescens* strain XJ3 is applied to *Poa annua* L. seed planted in the fall of 2011 shoot mass is inhibited by 51% and root mass by 50%. *P. fluorescens* strain XJ3 inhibit *Poa annua* L. shoot mass by 69% and root mass by 75%. *P. fluorescens* strain LRS12 is applied to the furrow containing *Poa annua* L. seed only in the fall of 2012. *P. fluorescens* strain LRS12 inhibit *Poa annua* L. the least amount; shoot mass is inhibited by 42%, and root mass is inhibited by 39%. These three bacteria isolates tested in the field do not inhibit the growth of Kentucky bluegrass cultivar 'NuGlade" and winter wheat cultivar 'Madsen' in the field trials (data not shown).

TABLE 6

Field test data from application of weed-suppressive bacteria to annual blue grass seeded in meter rows.

| Strain | Year | Shoot Control g m$^{-1}$ | Shoot Bacteria g m$^{-1}$ | Shoot % Inhibition % | Root Control g m$^{-1}$ | Root Bacteria g m$^{-1}$ | Root % Inhibition % |
|---|---|---|---|---|---|---|---|
| P.f. strain XJ3 | 2011-2012 | 3.23 | 1.58 | 51 | 4.27 | 2.13 | 50 |
| NRRL B-50851 | 2012-2013 | 5.24 | 1.65 | 69 | 7.92 | 1.98 | 75 |
| P.f. strain XS18 | 2011-2012 | 3.81 | 2.12 | 44 | 5.24 | 1.34 | 74 |
| NRRL B-50852 | 2012-2013 | 4.6 | 1.01 | 78 | 6.77 | 1.40 | 79 |
| P.f. strain LRS12 | 2011-2012 | nd | nd | | nd | nd | |
| NRRL B-50853 | 2012-2013 | 2.32 | 1.34 | 42 | 4.42 | 2.71 | 39 |

Example 6

Rice as an Agriculturally Acceptable Carrier

One can coat rice (an agriculturally acceptable carrier) with the one or more bacteria described herein to form the biocontrol agent of this invention. One can broadcast the bacteria-coated rice in the fall of the year into moisture, and the rice will distribute the bacterium throughout the surface of the soil. Alternatively, the bacteria-coated rice can be broadcast at any time prior to rain or application of water (irrigate) to the area where the coated rice are broadcasted.

To generate this bacteria-coated rice biocontrol agent, *P. fluorescens* strain XJ3 (NRRL B-50851) is grown in PMS broth to $10^8$ cells/L. Then, 10 oz. media per 60 pounds of rice are mixed together to form a slurry and are rotated in a drum at 25° C. until the rice absorbs the media. After the rice is dry, the bacteria-coated rice is broadcast distributed onto the land to be treated at 30 pounds per acre. When the *P. fluorescens* strain XJ3 (NRRL B-50851)-coated rice is applied to a field test per Example 5, above, similar results are expected as described in Table 6.

Alternatively, after culturing *P. fluorescens* strain XJ3 (NRRL B-50851) in PMS media to a density of $10^8$ cells/L, the media is centrifuged to pellet the bacteria and the liquid is decanted. The bacteria are freeze-dried to obtain a density of $2 \times 10^8$ cells/g. Then, 2 g freeze-dried bacteria are mixed with 30 pounds per acre of rice and water to form a slurry. This slurry is rotated in a drum until all liquid is absorbed by the rice. After the bacteria-coated rice are dry, one can direct drill or broadcast the bacteria-coated rice at 30 pounds per acre.

Example 7

Pellets of Wheat Flour and *P. fluorescens* Strain XJ3 (NRRL B-50851)

One can mix wheat flour (an agriculturally acceptable carrier) with finely ground plant residue and add one or more bacteria described herein, extrude the mixture of various diameters, and cut the strings of bacteria into different lengths to form the biocontrol agent of this invention. One can broadcast the bacteria-embedded pellets or prills in the fall of the year into moisture, and the pellets or prills will distribute the bacterium throughout the surface of the soil. Alternatively, the bacteria-embedded pellets or prills can be broadcast at any time prior to rain or application of water (irrigate) to the area where the pellets or prills are broadcasted.

To generate these pellets or prills embedded with the biocontrol agent, *P. fluorescens* strain XJ3 (NRRL B-50851) is grown in PMS broth to $10^8$ cells/mL. One can mix 454 g of a matrix, such as wheat or plant flour together with 200 to 300 g of a coarser matrix of finely ground plant residue or other materials. To the flour/residue mixture, 250 to 350 mL of bacterial broth is added to bring the material into a stiff ball. The amount of broth needed will vary with the absorptive capacity of the materials. The flour, residue, bacteria mixture is extruded through holes of various diameter and cut to the width needed for the given application. After the pellets are dry, the bacterial pellets are broadcast distributed onto the land so that $10^{14}$ cells are distributed per acre.

Alternately, one gram of freeze-dried bacteria can be added to the dry mixture and 250 to 350 mL of water can be added to the flour, residue, bacteria mixture. After culturing *P. fluorescens* strain XJ3 (NRRL B-50851) in KB media to a density of $10^8$ cells/L, the media is centrifuged to pellet the bacteria and the liquid is decanted. The bacteria are freeze-dried to obtain a density of $4 \times 10^{13}$ cells/g. Then, 2 g freeze-dried bacteria are mixed with 454 g of flour/residue mixture and 250 to 350 mL of water is added to the flour, residue, and bacteria mixture. The material is mixed to bring the material into a stiff ball. The flour, residue, and bacteria mixture is extruded through holes of various diameter and cut to the width needed for the given application. After the bacterial embedded pellets are dry, one can broadcast the pellets to obtain $10^{14}$ cells per acre.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

I, the inventor, claim as follows:

1. A method for controlling the growth of annual bluegrass and/or rough bluegrass in an area in need of treatment comprising applying a biocontrol agent effective for controlling annual bluegrass and rough bluegrass root growth and germination comprising one or more *Pseudomonas fluorescens* strains that inhibit annual bluegrass and/or rough bluegrass root growth and seed germination, wherein said one or more *P. fluorescens* strains are selected from the group consisting of *P. fluorescens* biovar B strain XJ3 (NRRL B-50851), *P. fluorescens* biovar B strain XS18 (NRRL B-50852), *P. fluorescens* biovar A strain LRS12 (NRRL B-50853), and combinations thereof in an amount effective to control the growth of annual bluegrass and/or rough bluegrass to said area in need of treatment.

2. The method of claim 1 wherein said amount of said *P. fluorescens* is between approximately $10^5$ to approximately $10^{11}$ cfu bacteria per square meter of said area in need of treatment.

3. The method of claim 1 wherein application of said biocontrol agent occurs after rain or irrigation of the area in need of treatment, prior to irrigating said area in need of treatment, or when rain is anticipated.

4. The method of claim 1 wherein the air temperature in said area in need of treatment is between approximately 32° F. and approximately 70° F.

5. The method of claim 4 wherein said air temperature is between approximately 32° F. and approximately 50° F.

6. The method of claim 1 wherein said biocontrol agent is applied to bare soil or plants.

7. The method of claim 1 wherein said biocontrol agent is applied via spraying, broadcasting, or injecting into the soil.

8. A method for controlling the growth of annual bluegrass and/or rough bluegrass in an area in need of treatment comprising applying an agriculturally acceptable carrier, a biocontrol agent, optionally a herbicide, and optionally a fertilizer, in an amount effective to control the growth of annual bluegrass and/or rough bluegrass to said area in need of treatment; wherein said biocontrol agent comprises one or more *Pseudomonas fluorescens* strains selected from the group consisting of *P. fluorescens* biovar B strain XJ3 (NRRL B-50851), *P. fluorescens* biovar B strain XS18 (NRRL B-50852), and *P. fluorescens* biovar A strain LRS12 (NRRL B-50853).

9. The method of claim 8, wherein said agriculturally acceptable carrier is selected from the group consisting of seed, rice, talc, carbohydrate, polysaccharide, polymeric porous material, milk, water, medium, and pellet made from a cereal grain flour or meal.

10. The method of claim 8, wherein said amount of said *P. fluorescens* is between approximately $10^5$ to approximately $10^{11}$ cfu bacteria per square meter of said area in need of treatment.

11. The method of claim 8, wherein application of said biocontrol agent occurs after rain or irrigation of the area in need of treatment, prior to irrigating said area in need of treatment, or when rain is anticipated.

12. The method of claim 8, wherein the air temperature in said area in need of treatment is between approximately 32° F. and approximately 70° F.

13. The method of claim 12, wherein said air temperature is between approximately 32° F. and approximately 50° F.

14. The method of claim 8, wherein said biocontrol agent is applied to bare soil or plants.

15. The method of claim 8, wherein said biocontrol agent is applied via spraying, broadcasting, or injecting into the soil.

* * * * *